US010234379B2

(12) United States Patent
Ogawa et al.

(10) Patent No.: US 10,234,379 B2
(45) Date of Patent: Mar. 19, 2019

(54) ELECTROMAGNETIC WAVE DETECTOR, ELECTROMAGNETIC WAVE DETECTOR ARRAY, AND GAS ANALYZING APPARATUS

(71) Applicant: Mitsubishi Electric Corporation, Chiyoda-ku (JP)

(72) Inventors: Shimpei Ogawa, Chiyoda-ku (JP); Daisuke Fujisawa, Chiyoda-ku (JP)

(73) Assignee: Mitsubishi Electric Corporation, Chiyoda-ku (JP)

( * ) Notice: Subject to any disclaimer, the term of this patent is extended or adjusted under 35 U.S.C. 154(b) by 16 days.

(21) Appl. No.: 15/549,200

(22) PCT Filed: Mar. 9, 2016

(86) PCT No.: PCT/JP2016/057265
§ 371 (c)(1),
(2) Date: Aug. 7, 2017

(87) PCT Pub. No.: WO2016/167052
PCT Pub. Date: Oct. 20, 2016

(65) Prior Publication Data
US 2018/0067041 A1    Mar. 8, 2018

(30) Foreign Application Priority Data

Apr. 15, 2015 (JP) .................. 2015-083342

(51) Int. Cl.
*G01N 21/35* (2014.01)
*G01N 21/3504* (2014.01)
*H01L 35/32* (2006.01)
*H01L 37/02* (2006.01)
*G01J 5/00* (2006.01)
*H01L 27/16* (2006.01)
*G01J 5/08* (2006.01)
*G01J 5/02* (2006.01)
(Continued)

(52) U.S. Cl.
CPC ........ *G01N 21/3504* (2013.01); *G01J 5/0014* (2013.01); *G01J 5/023* (2013.01);
(Continued)

(58) Field of Classification Search
CPC .......... G01J 5/0014; G01J 5/023; G01J 5/024; G01J 5/0862; G01J 5/10; G01J 5/20;
(Continued)

(56) References Cited

U.S. PATENT DOCUMENTS

2006/0169902 A1    8/2006 Watanabe
2012/0050743 A1    3/2012 Yanai et al.
(Continued)

FOREIGN PATENT DOCUMENTS

JP    2005-172762 A    6/2005
JP    2006-214758 A    8/2006
(Continued)

OTHER PUBLICATIONS

International Search Report dated Jun. 7, 2016 in PCT/JP2016/057265 filed Mar. 9, 2016.
(Continued)

*Primary Examiner* — Marcus H Taningco
(74) *Attorney, Agent, or Firm* — Oblon, McClelland, Maier & Neustadt, L.L.P.

(57) ABSTRACT

An electromagnetic wave detector that selectively detects electromagnetic waves of wavelength λA includes a temperature detection unit that includes: a substrate including a cavity portion; a wavelength selection structure that generates a surface plasmon resonance with an electromagnetic wave of a predetermined wavelength λA for converting to heat and absorbing, and a detection film that detects the absorbed heat; and a support structure that retains the temperature detection unit above the cavity portion; wherein the support structure further includes a reflection structure that reflects the electromagnetic waves of the absorption wavelength of the support structure.

20 Claims, 9 Drawing Sheets

(51) Int. Cl.
    *G01J 5/10*    (2006.01)
    *G01J 5/20*    (2006.01)
    *H01L 27/146*  (2006.01)
    *G01N 21/25*       (2006.01)

(52) U.S. Cl.
    CPC ............ *G01J 5/024* (2013.01); *G01J 5/0862* (2013.01); *G01J 5/10* (2013.01); *G01J 5/20* (2013.01); *H01L 27/14649* (2013.01); *H01L 27/16* (2013.01); *H01L 35/32* (2013.01); *H01L 37/02* (2013.01); *G01N 2021/258* (2013.01)

(58) Field of Classification Search
    CPC .......... G01N 2021/258; G01N 21/3504; H01L 27/14649; H01L 27/16; H01L 35/32; H01L 37/02
    See application file for complete search history.

(56) References Cited

U.S. PATENT DOCUMENTS

| | | | |
|---|---|---|---|
| 2014/0175284 A1* | 6/2014 | Roh | G01J 5/0853 250/338.4 |
| 2014/0226021 A1 | 8/2014 | Koechlin et al. | |
| 2014/0319359 A1* | 10/2014 | Sasaki | G01J 5/20 250/353 |
| 2014/0353506 A1* | 12/2014 | Nam | G01J 5/20 250/349 |
| 2016/0153837 A1 | 6/2016 | Kakimoto et al. | |
| 2016/0356652 A1* | 12/2016 | Yun | G01J 5/20 |

FOREIGN PATENT DOCUMENTS

| | | |
|---|---|---|
| JP | 2009-156614 A | 7/2009 |
| JP | 2011-95137 A | 5/2011 |
| JP | 2012-52910 A | 3/2012 |
| JP | 2013-44703 A | 3/2013 |
| JP | 2014-32088 A | 2/2014 |
| JP | 2014-521094 A | 8/2014 |
| WO | 2014/199583 A1 | 12/2014 |

OTHER PUBLICATIONS

Japanese Office Action dated Nov. 1, 2016 in Japanese Patent Application 2016-554894 (with partial English-language translation).

* cited by examiner

US 10,234,379 B2

ELECTROMAGNETIC WAVE DETECTOR, ELECTROMAGNETIC WAVE DETECTOR ARRAY, AND GAS ANALYZING APPARATUS

TECHNICAL FIELD

The present invention relates to an electromagnetic wave detector, an electromagnetic wave detector array, and a gas analyzing apparatus. In particular, the invention relates to an electromagnetic wave detector, an electromagnetic wave detector array, and a gas analyzing apparatus which selectively detect an electromagnetic wave of a specific wavelength by converting the electromagnetic wave into heat.

BACKGROUND ART

A home appliance such as an air conditioner needs to include a sensitive and simple electromagnetic wave detector which detects the position of a human body or temperature distribution in a room, in order to realize power saving operation and comfortable temperature control. As such an electromagnetic wave detector, an infrared sensor called a thermal infrared sensor or a uncooled infrared sensor is used particularly for detecting an infrared ray. The infrared sensor detects an incident infrared ray by absorbing the infrared ray, converting the infrared ray into heat, and converting the heat into an electric signal. The thermal infrared sensor uses a structure where an infrared ray-absorption unit is held in midair by a support leg and, thus, the thermal insulation property of the infrared-ray absorption unit is improved and a change in temperature of an electromagnetic wave absorption unit is read highly accurately.

For example, in a thermopile infrared sensor including a thermocouple, a hot junction of the thermocouple is provided above a cavity portion, and a cold junction of the thermocouple is provided on a frame body which surrounds the cavity portion. The temperature of the hot junction is detected from a thermoelectromotive force generated due to the difference in temperature between the hot junction and the cold junction. Sensitivity of the thermopile infrared sensor is improved, for example, by reducing thermal capacity of the hot junction, reducing thermal conductivity from the hot junction to the cold junction, and increasing absorption by an electromagnetic-wave absorbing film (for example, see Patent Document 1).

PRIOR ART DOCUMENT

Patent Document

Patent Document 1: JP 2005-172762 A

SUMMARY OF THE INVENTION

Problems to be Solved by the Invention

In a case where a wavelength of an infrared ray to be detected is selected in a conventional electromagnetic wave detector, formation of an infrared-ray absorbing film, which selectively absorbs an infrared ray in a predetermined wavelength band into an infrared-ray absorption unit (temperature sensor unit), enables the electromagnetic wave detector to have selectivity in the detection wavelength. However, infrared-ray absorption also occurs at a support structure, for example, a support leg (for example, an insulating film, wiring, and a thermocouple which form the support leg), which holds the infrared-ray absorption unit above the cavity portion. There is a problem that non-selective infrared-ray absorption at the support leg deteriorates wavelength selectivity of the electromagnetic wave detector.

In view of the foregoing, an object of the present invention is to provide an electromagnetic wave detector which prevents non-selective electromagnetic wave absorption at a support leg or the like and has high selectivity in a detection wavelength band.

Means for Solving the Problems

An aspect of the present invention is an electromagnetic wave detector which selectively detects an electromagnetic wave of a wavelength $\lambda A$, the electromagnetic wave detector including:
  a substrate which has a cavity portion;
  a temperature detection unit which includes
    a wavelength selection structure that generates a surface plasmon resonance with an electromagnetic wave of the wavelength $\lambda A$ which is predetermined, converts the electromagnetic wave into heat, and absorbs the heat, and
    a detection film that detects the heat having been absorbed; and
  a support structure which holds the temperature detection unit above the cavity portion, wherein
  the support structure further includes a reflection structure which reflects an electromagnetic wave of an absorption wavelength of the support structure.

Effects of the Invention

According to the electromagnetic wave detector according to the present invention, an electromagnetic wave detector which can detect only electromagnetic waves of a predetermined wavelength with high sensitivity.

EMBODIMENTS OF THE INVENTION

In the embodiments of the present invention, electromagnetic wave detectors will be described using infrared light (also referred to as an infrared ray) as detection light; however, an electromagnetic wave detector according to the present invention is also effective for detection of electromagnetic waves other than infrared light, such as ultraviolet light, near-infrared light, a terahertz (THz) wave, a microwave, and the like. Note that in the embodiments according to the present invention, the above light and radio waves are collectively referred to as electromagnetic waves.

A surface plasmon resonance phenomenon or a plasmon resonance phenomenon which is interaction between a metal surface and light, a phenomenon called pseudo surface plasmon resonance which refers to a resonance phenomenon of light outside the visible-light range and the near-infrared light range on a metal surface, and a phenomenon called a metasurface, a metamaterial or a plasmonic metamaterial which enables manipulation of a specific wavelength due to the structure of the metasurface, the metamaterial, or the plasmonic metamaterial with a dimension less than or equal to the specific wavelength are not distinguished from one another by terms, but are treated equal from the viewpoint of effects caused by the phenomena. Here, each resonance described above is referred to as surface plasmon resonance or plasmon resonance, or is simply referred to as resonance.

Note that as a material for generating plasmon resonance, a metal with a negative dielectric constant, such as gold, silver, aluminum, copper, or the like, or graphene, is preferable. In addition, in the embodiments of the present invention, a SOI (Silicon-on-Insulator) diode electromagnetic wave detector will be mainly described; however, the present invention can also be applied to another thermal infrared sensor such as a bolometer, a thermopile sensor, or a pyroelectric sensor.

First Embodiment

Figure 1:
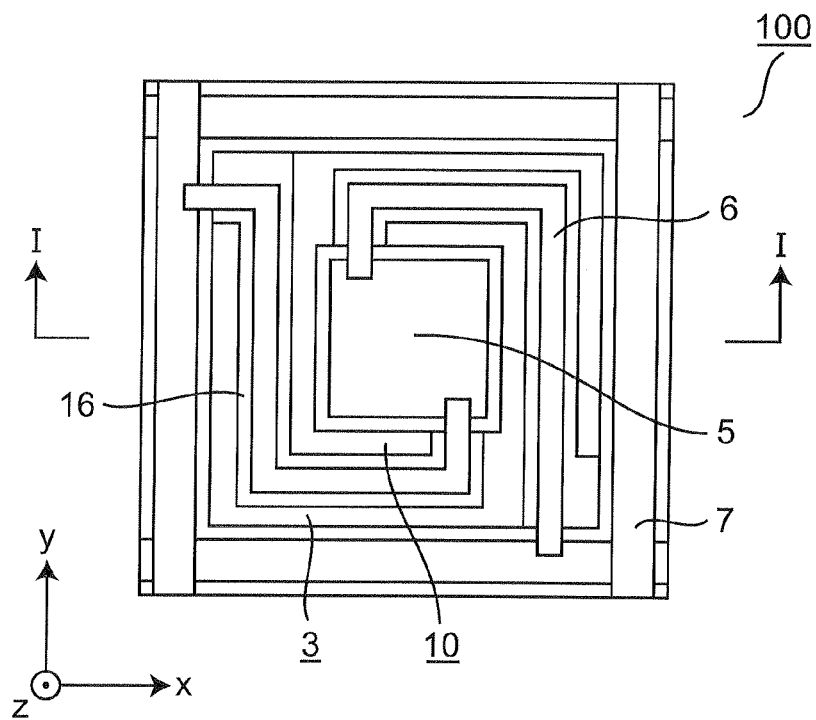
FIG. 1 is a top view of an electromagnetic wave detector according to a first embodiment of the present invention.
Figure 2:
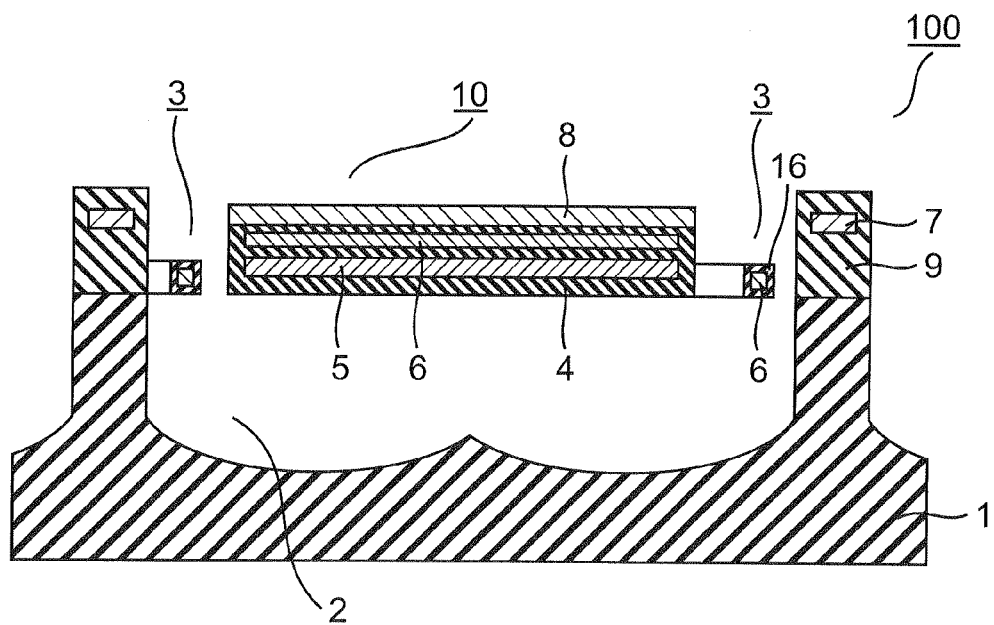
FIG. 2 is a cross-sectional view of the electromagnetic wave detector in FIG. 1 viewed in I-I direction.

FIG. 1 is a top view of a thermal-type electromagnetic wave detector according to a first embodiment of the present invention, entirety of which is denoted by 100. FIG. 2 is a cross-sectional view of the electromagnetic wave detector 100 (including an absorption body and the like) in FIG. 1 viewed in I-I direction. Note that, in FIG. 1, a detection film 5 and thin-film metal wiring 6 and 7, which usually are not seen, are illustrated as if the detection film 5 and the thin-film metal wiring 6, 7 were seen.

As illustrated in FIG. 2, the electromagnetic wave detector 100 includes a substrate 1 made of, for example, silicon. The substrate 1 is provided with a cavity portion 2, and a temperature detection unit 10 is supported above the cavity portion 2 by a support leg 3. Here, there are two support legs 3, and as illustrated in FIG. 1, the support leg 3 has a bridge shape bent in an L-shape when seen from above; however, the support leg 3 is not limited to this. The support leg 3 includes the thin-film metal wiring 6 and a dielectric layer 16 which supports the thin-film metal wiring 6. The thin-film metal wiring 6 is made of, for example, titanium. The dielectric layer 16 is made of, for example, silicon oxide.

A dielectric layer 9 made of, for example, silicon oxide is provided around the cavity portion 2. Aluminum wiring 7 is provided in the dielectric layer 9. The aluminum wiring 7 is connected to a detection circuit (not illustrated).

The temperature detection unit 10 includes a dielectric layer 4 made of, for example, silicon oxide. The detection film 5 and the thin-film metal wiring 6 are provided in the dielectric layer 4. The detection film 5 is made of, for example, a diode including crystalline silicon. The temperature detection unit 10 further includes a wavelength selection structure 8 provided on the dielectric layer 4. The wavelength selection structure 8 is made of a metal, and a plurality of recesses is provided on the upper side of the wavelength selection structure 8.

Figure 3:
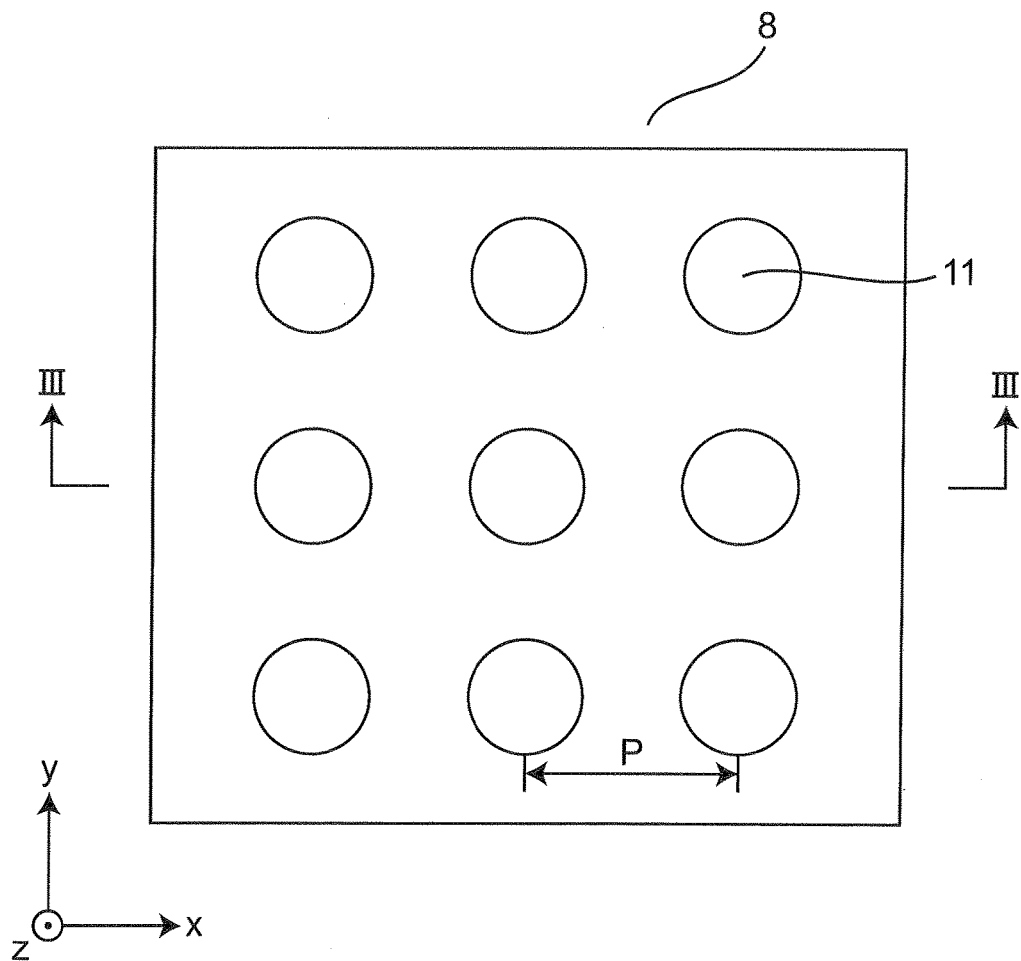
FIG. 3 is a top view of a wavelength selection structure of the electromagnetic wave detector according to the first embodiment of the present invention.
Figure 4:
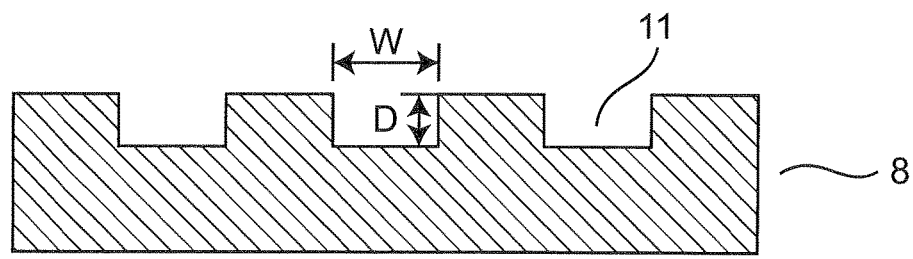
FIG. 4 is a cross-sectional view of the wavelength selection structure in FIG. 3 viewed in direction.

FIG. 3 is a top view of the wavelength selection structure 8, and FIG. 4 is a cross-sectional view of the wavelength selection structure 8 in FIG. 3 viewed in direction.

As illustrated in FIGS. 3 and 4, the wavelength selection structure 8 is a structure where recesses or projections are periodically formed on the upper side of a metal layer in order to cause surface plasmon resonance, and only a specific resonance wavelength is converted into heat and is absorbed. Specifically, as illustrated in FIG. 3, in the wavelength selection structure 8, the periodic recesses 11 are arranged in two-dimensional directions. Here, the recesses 11 are arranged in a 3×3 matrix; however, the wavelength selection structure 8 is not limited to this.

The wavelength selection structure 8 is made of a metal which generates surface plasmon resonance, and is made of, for example, gold, silver, aluminum, or copper. The film thickness of the wavelength selection structure 8 may be any thickness as long as infrared light of a wavelength which is selectively absorbed does not leak under the wavelength selection structure 8. If the film thickness is satisfied, the layer under the metal layer does not affect plasmon resonance. Therefore, the layer may be an insulator layer or a semiconductor layer.

For example, in order to detect infrared light with a wavelength of 10 μm, the recess 11 has, for example, a cylindrical shape with diameter W of 6 μm, depth D of 1.5 μm, and an arrangement pitch P of the recesses 11 is, for example, 10 μm. In FIG. 3, the cross-section of the recess 11 in x-y plane (horizontal cross-section) is circular; however, the cross-section may be elliptical, square, rectangular, polygonal, or the like. Note that an elliptical or a rectangular cross-section of the recess 11 allows only a specific polarized light to be absorbed. In addition, the pitch P of the recesses 11 preferably matches the wavelength of an electromagnetic wave to be selectively absorbed. In addition, here, the recesses 11 are arranged in a matrix (two-dimensionally); however, the recesses 11 may be arranged one-dimensionally. One-dimensional arrangement of the recesses 11 allows only a specific polarized light to be detected.

Figure 5:
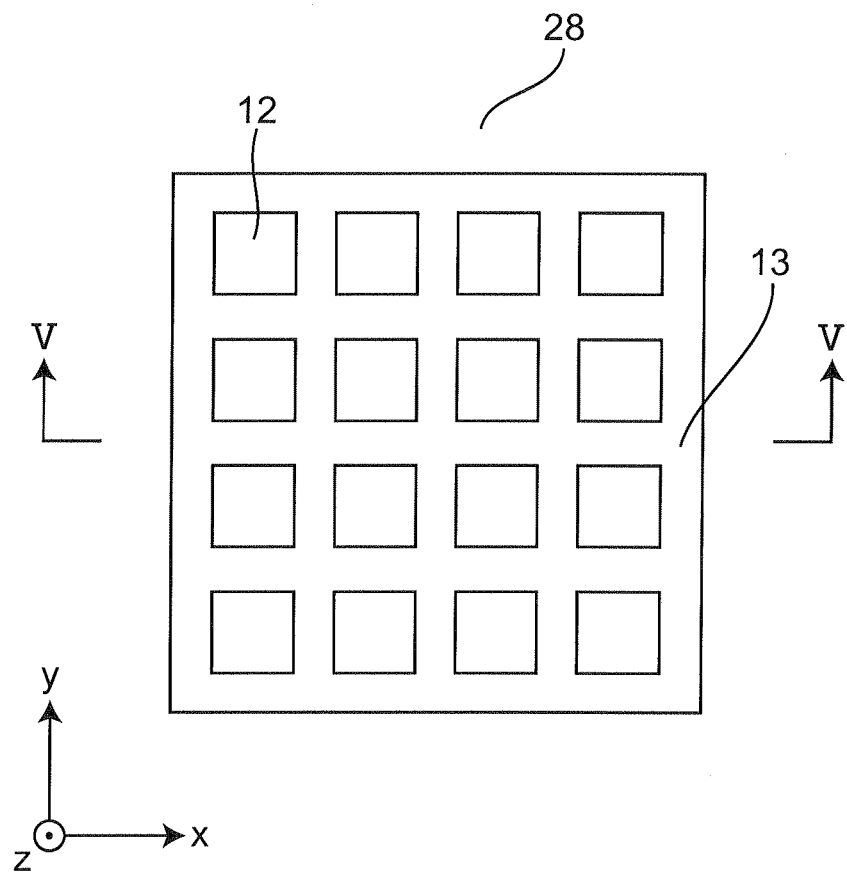
FIG. 5 is a top view of another wavelength selection structure according to the first embodiment of the present invention.
Figure 6:
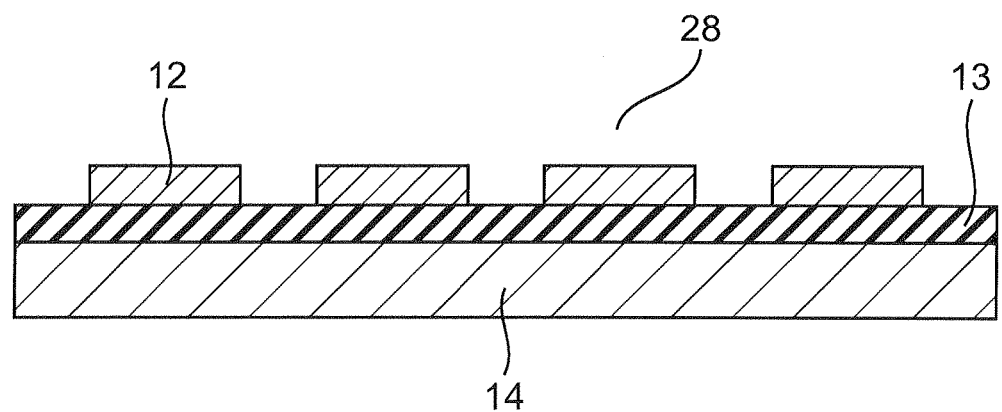
FIG. 6 is a cross-sectional view of the wavelength selection structure in FIG. 5 viewed in V-V direction.

FIG. 5 is a top view of another wavelength selection structure 28 used for the electromagnetic wave detector 100. FIG. 6 is a cross-sectional view of the wavelength selection structure 28 in FIG. 5 viewed in V-V direction. In the wavelength selection structure 28, an intermediate layer 13 is provided on a metal layer 14, and metal patterns 12 are provided on the intermediate layer 13. The metal layer 14 is made of, for example, aluminum, or gold. The intermediate layer 13 is made of an insulator or a dielectric such as silicon oxide or a semiconductor such as silicon or germanium. By selecting the material of the intermediate layer 13, it is possible to control the detection wavelength, the number of detection wavelengths, and the bandwidth of the detection wavelength.

The metal pattern 12 may be formed of a metal such as gold, silver, or aluminum, and in addition, may be formed of graphene, which is not a metal. In a case where the metal pattern 12 is formed of graphene, the film thickness can be as thin as thickness of one atomic layer. Therefore, the thermal time constant can be decreased and high-speed operation is made possible.

By changing the size of the metal pattern 12 (dimensions in x and y directions in FIG. 5), it is possible to control the wavelength at which plasmon resonance occurs. Therefore, by changing the size of the metal pattern 12, the absorption wavelength can be selected. In addition, in FIG. 5, the metal patterns 12 are arranged in a matrix (two-dimensionally) at predetermined pitches; however, the metal patterns 12 may be arranged one-dimensionally.

Note that in addition to the above structures, a structure of selectively absorbing only a specific wavelength by laminating dielectric layers made of silicon oxide or silicon nitride may be used as the wavelength selection structure.

As illustrated in FIG. 2, the support leg 3 is configured to include the dielectric layer 16 made of, for example, silicon oxide, and the thin-film metal wiring 6 is formed in the dielectric layer 16. The thin-film metal wiring 6 electrically connects the detection film 5 of the temperature detection unit 10 and the aluminum wiring 7. The thin-film metal wiring 6 is made of, for example, a titanium alloy having a thickness of 100 nm. An electric signal output from the detection film 5 passes through the thin-film metal wiring 6 formed in the support leg 3, is transmitted to the aluminum wiring 7, and is read by the detection circuit (not illustrated). Electrical connection between thin-film metal wiring 6 and the detection film 5 and electrical connection between the thin-film metal wiring 6 and the aluminum wiring 7 may be made via a conductor (not illustrated) extending in the vertical direction, as necessary.

In a case where a support leg 3 is configured to include a thin-film metal wiring 6 and a dielectric layer 16 as in a conventional structure, since infrared light is also incident on the support leg 3, infrared light is absorbed by the dielectric layer 16 of the support leg 3. For example, in a case where the dielectric layer 16 of the support leg 3 is formed of silicon oxide or silicon nitride, infrared light with a wavelength of about 10 µm is absorbed by the dielectric layer 16.

Figure 7:
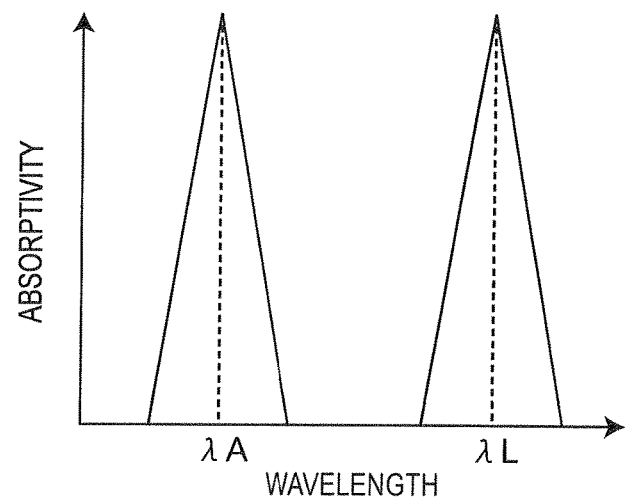
FIG. 7 illustrates electromagnetic wave absorption characteristics of an electromagnetic wave detector that has a support leg of a conventional structure.

FIG. 7 illustrates infrared light absorption characteristics of an electromagnetic wave detector including a support leg 3 configured to include a thin-film metal wiring 6 and a dielectric layer 16 as in the conventional structure. The abscissa axis indicates a wavelength, and the axis of ordinate indicates absorptivity. Infrared light with a wavelength of about $\lambda A$ is absorbed by a wavelength selection structure 8 of a temperature detection unit 10. In addition, since the dielectric layer 16 usually has an absorption wavelength in the infrared wavelength band (referred to as a wavelength $\lambda L$), infrared light with a wavelength of about the absorption wavelength is absorbed by the support leg 3. For example, in a case where the dielectric layer 16 is made of silicon oxide, infrared light with a wavelength of around 10 µm is absorbed. As a result, there is a problem that detection-wavelength selectivity lowers and detection sensitivity of infrared light of the wavelength $\lambda A$ lowers.

Figure 8:
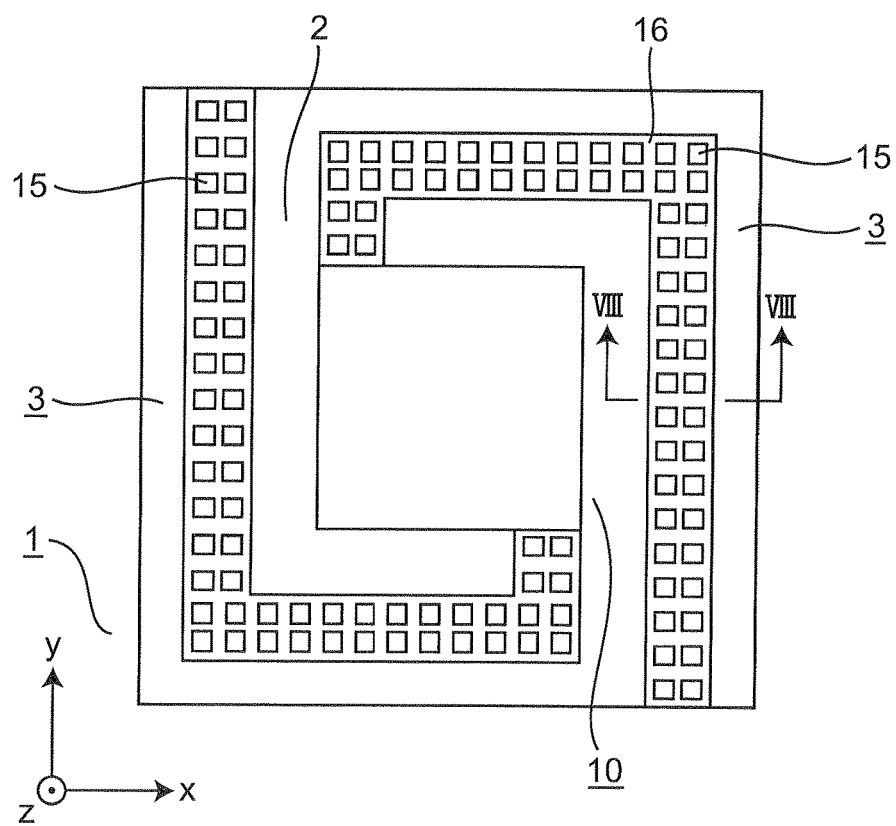
FIG. 8 is a top view of the electromagnetic wave detector according to the first embodiment of the present invention.
Figure 9:
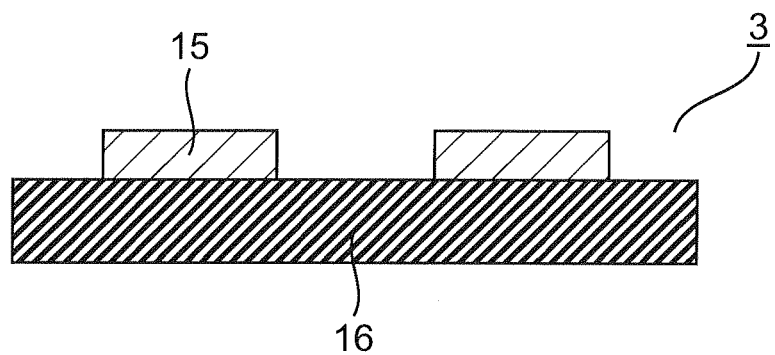
FIG. 9 is a cross-sectional view of a support leg of the electromagnetic wave detector in FIG. 8 viewed in VIII-VIII direction.

In contrast, in the electromagnetic wave detector 100 according to the first embodiment of the present invention, the support leg 3 further includes a reflection structure as described above. FIG. 8 is a top view of the temperature detection unit 10 and the support legs 3 of the electromagnetic wave detector 100. FIG. 9 is a cross-sectional view of the support leg 3 in FIG. 8 viewed in VIII-VIII direction (the thin-film metal wiring 6 is not included in the view).

The reflection structure is made of, for example, metal patterns (patches) 15 formed on an upper side of the dielectric layer 16 as illustrated in FIG. 9. The metal patterns 15 generate surface plasmon resonance at a specific wavelength $\lambda p$ according to the pitch, the size and the interval of the metal patterns 15. This surface plasmon resonance intensifies reflection at a resonance wavelength. In addition, a reflection characteristic for the infrared wavelength band can be obtained when the film thickness of the metal pattern 15 is as thin as about 50 nm. Note that the upper side refers to a side where infrared light is incident, and a back side refers to a side which is opposite to the upper side.

Figure 10:
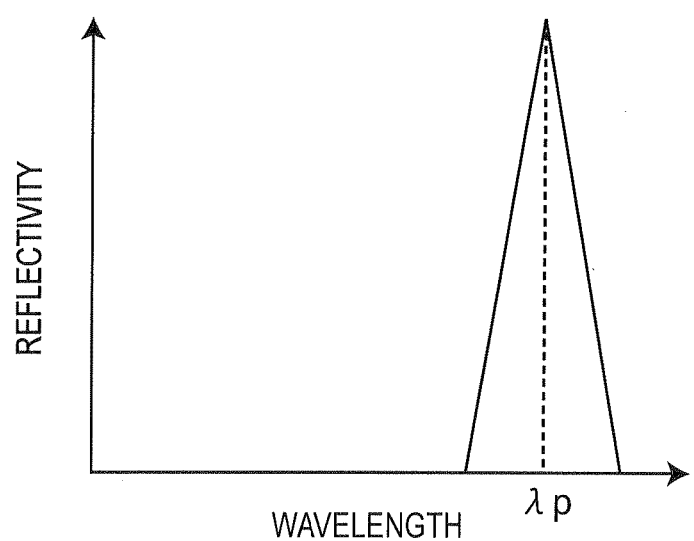
FIG. 10 illustrates a reflection characteristic of the support leg of electromagnetic wave detector according to the first embodiment of the present invention.

FIG. 10 illustrates an infrared-light reflection characteristic of the support leg 3 which has the reflection structure including the metal patterns 15. The abscissa axis indicates a wavelength, and the axis of ordinate indicates reflectivity. In FIG. 10, infrared light with a wavelength of about $\lambda p$ is selectively reflected. The reflection wavelength $\lambda p$ can be set to a desired wavelength by changing the pitch, the size, and the interval of the metal patterns 15. The horizontal cross-section of the metal pattern 15 may have, for example, a circular shape, a square shape, a rectangular shape, an elliptical shape, and a polygonal shape other than the above. By changing the shape of the horizontal cross-section, it is possible to select the wavelength of light which can be reflected. Note that the cross-section having a rectangular shape, an elliptical shape or the like enables polarization selectivity in reflected light.

For example, in a case where the shape in the horizontal cross-section of the metal pattern 15 is a square with a side of 2 µm, and two columns of the metal patterns 15 are arranged at a pitch of 3 µm, and gold is used as the material of the metal pattern 15, strong plasmon resonance occurs with respect to infrared light with a wavelength of around 10 µm. As a result, reflectivity of infrared light around 10 µm selectively increases (reflection wavelength $\lambda p=10$ µm).

As described above, in the dielectric layer 16 of the support leg 3 made of silicon oxide, absorption wavelength is about 10 µm (absorption wavelength $\lambda L=10$ µm). Therefore, since the support leg 3 has the reflection structure which reflects infrared light of about 10 µm (reflection wavelength $\lambda p=10$ µm) as in the electromagnetic wave detector 100 according to the first embodiment of the present invention, infrared light of about 10 µm is reflected by the reflection structure. Accordingly, the infrared light is not incident on the dielectric layer 16, and is not absorbed. That is, by providing the reflection structure such that the reflection wavelength $\lambda p$=the absorption wavelength $\lambda L$ is satisfied, detection-wavelength selectivity improves, and infrared light of the wavelength $\lambda A$ can be detected with high sensitivity.

Note that since the metal patterns 15 are discontinuously arranged on the dielectric layer 16, the thermal insulation property of the support leg 3 is not lowered. That is, thermal conductance of the support leg 3 is not increased. As a result, response speed of the electromagnetic wave detector 100 is not lowered.

In particular, absorption of infrared light by the support leg 3 is not considered conventionally. Therefore, since the reflection structure is used to prevent absorption of infrared light by the support leg 3, thermal conductance of the support leg 3 can be made small and sensitivity of the electromagnetic wave detector 100 can be improved.

Second Embodiment

Figure 11:
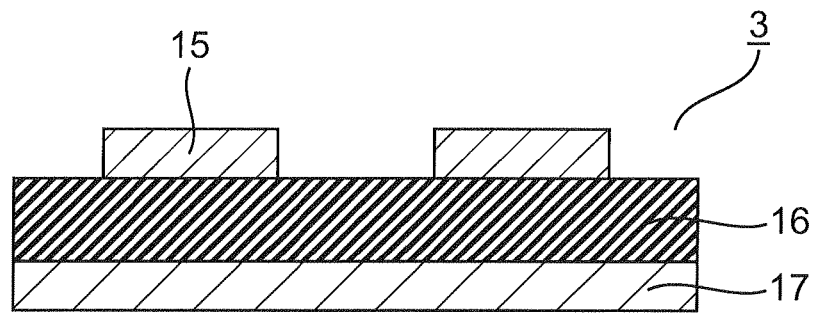
FIG. 11 is a cross-sectional view of another support leg of the electromagnetic wave detector according to the first embodiment of the present invention.

FIG. 11 is a cross-sectional view of a support leg 3 included in an electromagnetic wave detector according to a second embodiment of the present invention, viewed in a direction identical to VIII-VIII in FIG. 8 (thin-film metal wiring 6 is not included in the view). The electromagnetic wave detector is identical to the electromagnetic wave detector 100 according to the first embodiment except for the structure of the support leg 3.

As illustrated in FIG. 11, in the support leg 3 according to the second embodiment, similarly to the first embodiment, metal patterns 15 are provided on an upper side of a dielectric layer 16, a metal layer 17 is formed on a back side of the dielectric layer 16, and a MIM (Metal-Insulator-Metal) structure including three layers is formed. Plasmon resonance occurs in the MIM structure.

Similarly to the metal pattern 15, the metal layer 17 is made of a metal material with high reflectivity, such as gold, silver, aluminum, or the like. The film thickness of the metal layer 17 may be any thickness as long as infrared light with a wavelength at which plasmon resonance occurs in the MIM structure does not penetrate the metal layer 17.

Generally, in such a MIM structure, plasmon resonance is generated by infrared light of a specific wavelength depending on the arrangement (for example, the size, the pitch, or the thickness) of the metal patterns 15, and infrared light at the resonance wavelength is absorbed. However, in a case where the dielectric layer 16 sandwiched by the metal patterns 15 and a metal absorbs infrared light, infrared light at the absorption wavelength of the dielectric layer 16 is strongly reflected without being absorbed due to plasmon resonance.

Figure 12:
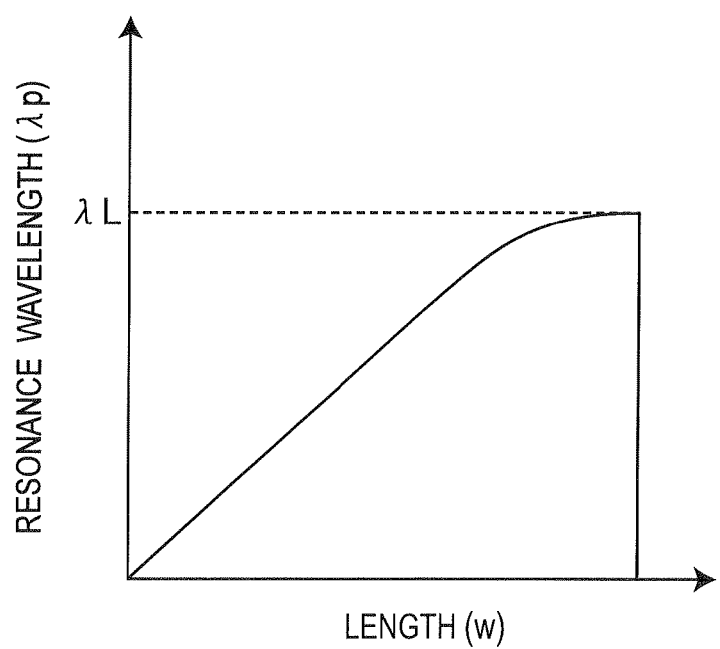
FIG. 12 illustrates a plasmon resonance characteristic of a support leg of a MIM structure according to a second embodiment of the present invention.
Figure 13:
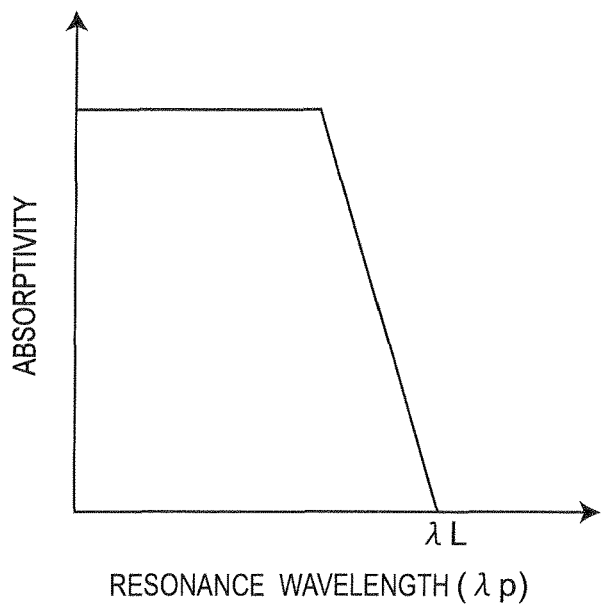
FIG. 13 illustrates an absorption characteristic of the support leg of the MIM structure according to the second embodiment of the present invention.

FIG. 12 illustrates a relationship between a length w of a side and a resonance wavelength $\lambda p$, the side being a side of a square of a horizontal cross-section of the metal pattern 15 in the support leg having the MIM structure. The axis of ordinate indicates the resonance wavelength $\lambda p$, and the abscissa axis indicates the length w of a side of the metal pattern 15. FIG. 13 illustrates a relationship between the absorption wavelength and the plasmon resonance wavelength $\lambda p$ in the support leg having the MIM structure. The axis of ordinate indicates absorptivity, and the abscissa axis indicates the plasmon resonance wavelength.

As illustrated in FIG. 12, as the length w of a side of the metal pattern 15 is longer, the resonance wavelength $\lambda p$ of plasmon resonance is longer. Then, as the resonance wavelength is closer to the absorption wavelength $\lambda L$ of the dielectric layer 16, the increase rate of the resonance wavelength decreases, and plasmon resonance does not occur at the time point when the reflection wavelength $\lambda q$=the absorption wavelength $\lambda L$ is satisfied.

That is, as illustrated in FIG. 13, by adjusting the length w of a side of the metal pattern 15 and making the resonance wavelength $\lambda p$ equal to the absorption wavelength $\lambda L$, of the dielectric layer 16, absorptivity of the support leg 3 can be reduced to 0.

As described, in the electromagnetic wave detector according to the second embodiment, since the support leg 3 has the MIM structure, absorption of infrared light by the support leg 3 can be prevented. As a result, detection-wavelength selectivity improves, and it is possible to detect infrared light of a specific wavelength with high sensitivity.

Note that in a case of a structure where an incident infrared ray is reflected by providing a reflective film which is separately held such that the reflective film is spaced from a support leg, without directly forming a reflection structure on the support leg, there is a space between the support leg and the reflective film. Therefore, because of stray light and/or multipath reflection, it is not possible to reflect all the incident infrared rays by the reflective film. In contrast, in a case of forming a special plasmon resonance structure in a support leg as in the present invention, infrared rays incident on the support leg at all incident angles can be reflected.

Third Embodiment

Figure 14:
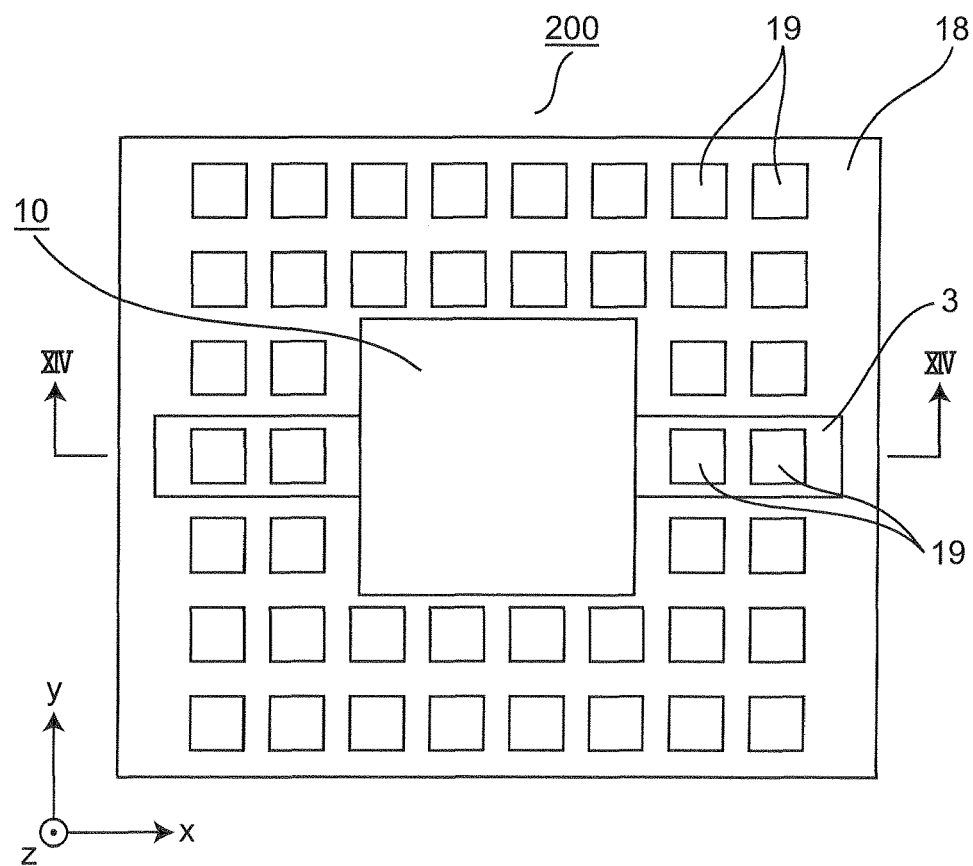
FIG. 14 is a top view of an electromagnetic wave detector according to a third embodiment of the present invention.
Figure 15:
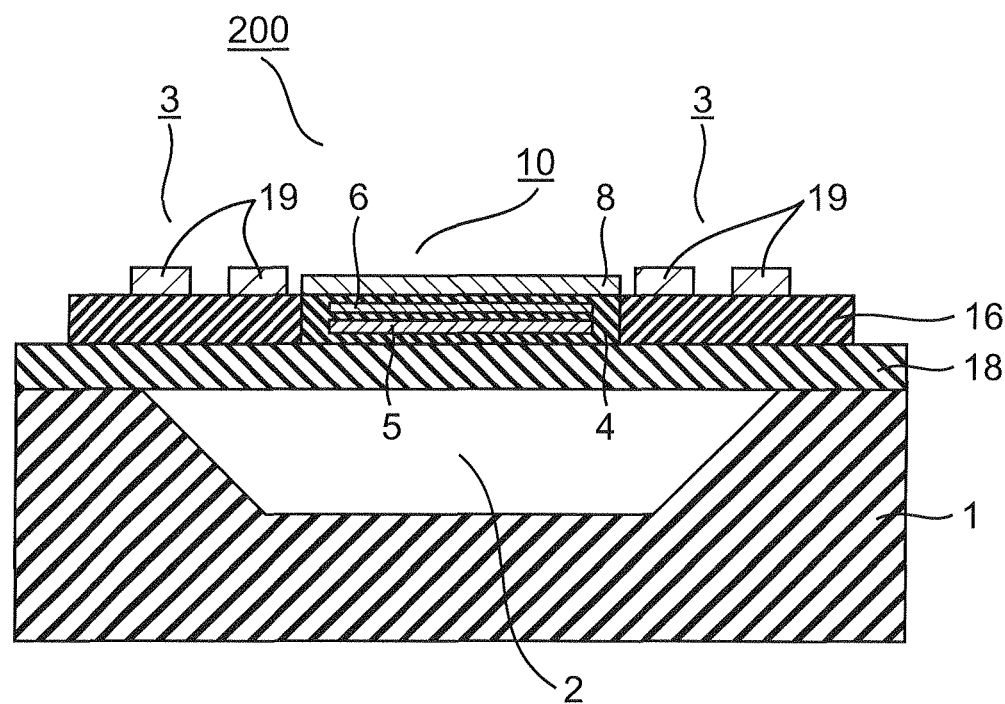
FIG. 15 is a cross-sectional view of the electromagnetic wave detector in FIG. 14 viewed in XIV-XIV direction.

FIG. 14 is atop view of an electromagnetic wave detector according to a third embodiment of the present invention, entirety of which is denoted by 200. FIG. 15 is a cross-sectional view of the electromagnetic wave detector 200 in FIG. 14 viewed in XIV-XIV direction. In FIGS. 14 and 15, reference symbols identical to those in FIGS. 1 and 2 denote identical or corresponding portions.

As illustrated in FIG. 15, the electromagnetic wave detector 200 includes a substrate 1 made of, for example, silicon. The substrate 1 is provided with a cavity portion 2. On the substrate 1, a membrane 18 formed of a thin film made of, for example, silicon oxide is provided. The periphery of the membrane 18 is fixed on the substrate 1 and the central portion of the membrane 18 is held above the cavity portion 2.

A temperature detection unit 10 and support legs 3 connected to the temperature detection unit 10 are provided on the membrane 18. The temperature detection unit 10 is held above the cavity portion 2 by the support legs 3 and the membrane 18.

The temperature detection unit 10 includes a dielectric layer 4 made of, for example, silicon oxide, and a detection film 5 and thin-film metal wiring 6 are provided in the dielectric layer 4. The detection film 5 is made of, for example, a diode including crystalline silicon. The temperature detection unit 10 further includes a wavelength selection structure 8 on the dielectric layer 4.

The support leg 3 may have a structure identical to that in the first embodiment, or may have a structure in which two conductors of a thermopile are provided in a dielectric layer 16. Since the temperature detection unit 10 is held by both the membrane 18 and the support legs 3 in the electromagnetic wave detector 200, the electromagnetic wave detector 200 can be more easily manufactured and the strength of the electromagnetic wave detector 200 is improved more than an electromagnetic wave detector having a structure of supporting a temperature detection unit 10 only by support legs 3.

In the electromagnetic wave detector 200, there is a problem that when infrared light is absorbed by the support legs 3 and the membrane 18, detection-wavelength selectivity lowers since infrared light is incident on the support legs 3 and the membrane 18 in addition to the temperature detection unit 10. Accordingly, detection sensitivity of infrared light of a predetermined wavelength lowers. To solve the problem, in the electromagnetic wave detector 200, as illustrated in FIG. 14, metal patterns 19 are provided on the support legs 3 and the membrane 18. As described above, the metal patterns 19 generate surface plasmon resonance at a specific wavelength λp depending on the pitch, the size, and the interval of the metal patterns 19, and reflects infrared light with a wavelength of about λp. In the electromagnetic wave detector 200, the pitch and the size of the metal patterns 19 are set so that infrared light of a wavelength absorbed by the support leg 3 and the membrane 18 is reflected.

As described, in the electromagnetic wave detector 200 according to the third embodiment, since the metal patterns 19 are provided on the support legs 3 and the membrane 18, it is possible to prevent absorption of infrared light by the support legs 3 and the membrane 18. As a result, selectivity in the detection wavelength improves, and infrared light of a specific wavelength can be detected with high sensitivity.

Note that the structure of providing the metal patterns 19 on the membrane 18 has been described here; however, for example, a MIM structure where a metal layer is further provided under the membrane 18, as illustrated in FIG. 11 of the second embodiment 2 may be adopted.

Fourth Embodiment

Figure 16:
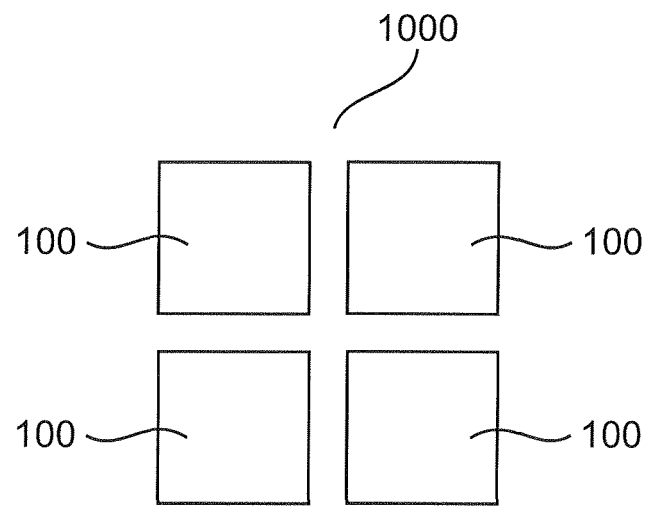
FIG. 16 is a top view of an electromagnetic wave detector array according to a fourth embodiment of the present invention.

FIG. 16 is a top view of an electromagnetic wave detector array according to a fourth embodiment of the present invention, the entire of which is denoted by 1000. In the electromagnetic wave detector array 1000, for example, a plurality of electromagnetic wave detectors 100 is arranged in a 2×2 matrix on a substrate (not illustrated). For example, electromagnetic wave detectors 100 in each row or column are selected by a scan circuit (not illustrated) provided outside, and information detected by each electromagnetic wave detector 100 is read in time series. Note that the electromagnetic wave detectors 100 are arranged in a 2×2 matrix here; however, arrangement of the electromagnetic wave detectors is not limited to this.

As described, since the electromagnetic wave detectors 100 selecting and detecting only a specific wavelength are arranged in a matrix to configure the electromagnetic wave detector array 1000, an image sensor which detects only a specific wavelength can be obtained. In particular, by preventing absorption of infrared light by the support leg 3 or the like, the electromagnetic wave detector array 1000 with high sensitivity can be obtained. Here, a matrix may be a two-dimensional arrangement or a one-dimensional line arrangement.

Note that the electromagnetic wave detectors 100 according to the first embodiment are arranged in a matrix here; however, other electromagnetic wave detectors such as the electromagnetic wave detectors 200 according to the third embodiment may be arranged in a matrix.

Fifth Embodiment

Figure 17:
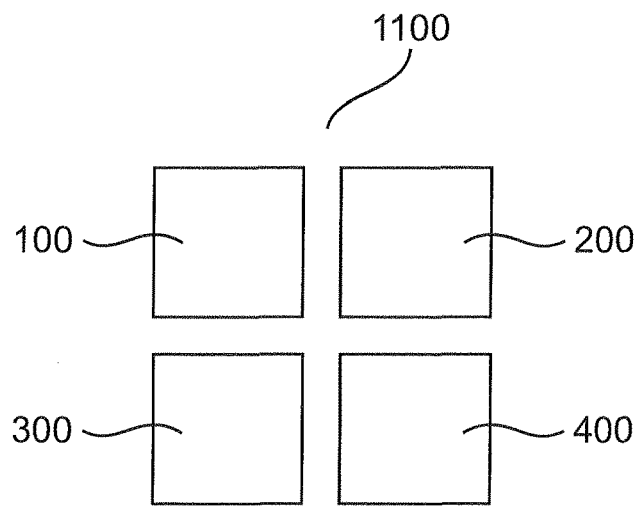
FIG. 17 is a top view of an electromagnetic wave detector array according to a fifth embodiment of the present invention.

FIG. 17 is atop view of an electromagnetic wave detector array according to a fifth embodiment of the present invention, entirety of which is denoted by 1100. In the electromagnetic wave detector array 1100, a plurality of electromagnetic wave detectors 100, 200, 300, and 400 with different detection wavelengths is arranged in a 2×2 matrix. Except for the arrangement, the electromagnetic wave detector array 1100 has a structure identical to that of the above-described electromagnetic wave detector array 1000.

Note that it is assumed, herein, that all the electromagnetic wave detectors have different detection wavelengths; however, for example, a plurality of the electromagnetic wave detectors 100 with an identical detection wavelength may be included. In addition, the electromagnetic wave detectors are, herein, arranged in a 2×2 matrix; however, the present embodiment is not limited to such arrangement.

As described, the electromagnetic wave detectors 100, 200, 300, and 400, each of which selects and detects only a specific wavelength, are arranged in a matrix to configure the electromagnetic wave detector array 1100. Therefore, it is possible, for example, to visually discriminate different types of gases as described later. In particular, by preventing absorption of infrared light by the support leg 3 or the like, the electromagnetic wave detector array with high sensitivity can be obtained.

Sixth Embodiment

Figure 18:
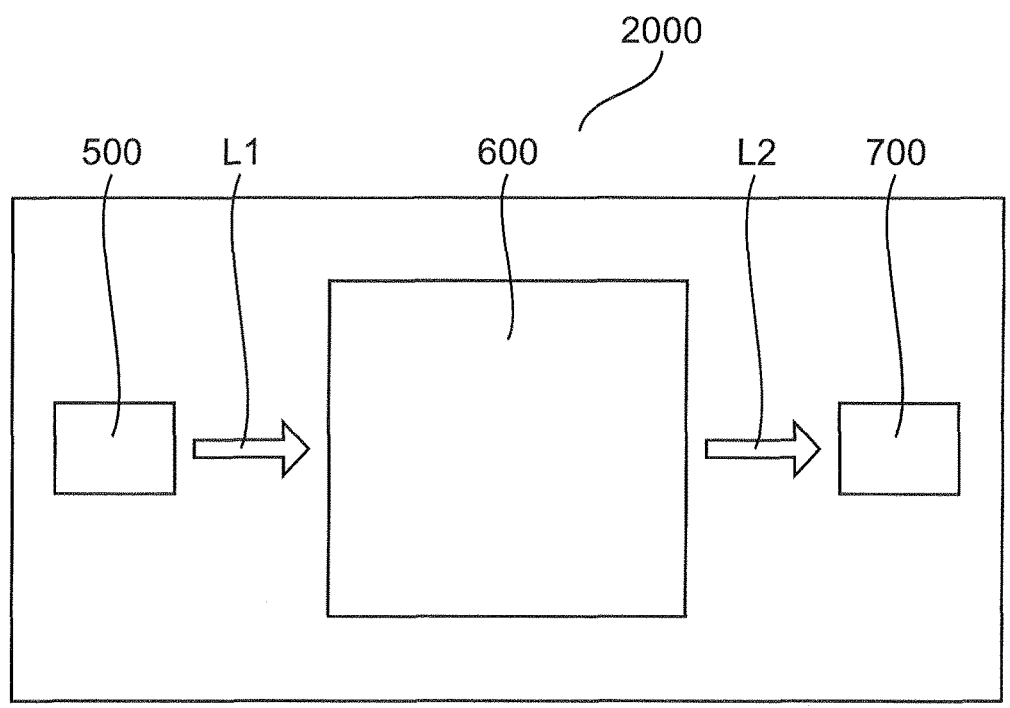
FIG. 18 is a schematic view of a gas analyzing apparatus according to a sixth embodiment of the present invention.

FIG. 18 is a schematic view of a gas analyzing apparatus according to a sixth embodiment of the present invention, entirety of which is denoted by 2000. The gas analyzing apparatus 2000 includes a light source 500 which emits an electromagnetic wave, a gas introduction mechanism (container) 600 which stores a gas serving as an analysis target, and an electromagnetic wave detector array 700 which receives an electromagnetic wave. For example, an electromagnetic wave detector array including a plurality of electromagnetic wave detectors with different detection wavelengths as illustrated in the fifth embodiment is used as the electromagnetic wave detector array 700; however, a single electromagnetism detector may be used. An electromagnetic wave L1 emitted from the light source 500 passes through a window (not illustrated) provided on the gas introduction mechanism 600, and a gas in the gas introduction mechanism 600 is irradiated with the electromagnetic wave L1. An electromagnetic wave L2 having passed through the gas inside the gas introduction mechanism 600 passes through, for example, another window (not illustrated) provided on the gas introduction mechanism 600, is incident on the electromagnetic wave detector array 700, and is detected.

In general, a gas has absorption peaks at a plurality of wavelengths including the infrared wavelength band. Therefore, if a gas is irradiated with an electromagnetic wave and an absorption peak of the gas is detected, the kind of the gas can be determined. The gas analyzing apparatus 2000 according to the sixth embodiment uses this property of gases to determine the kind of a gas. When an electromagnetic wave L1 passes through a gas filled in the gas introduction mechanism 600, the intensity of the electromagnetic wave L1 corresponding to an absorption wavelength of the gas lowers according to the concentration of the gas. Therefore, when the electromagnetic wave detector array 700 including a plurality of electromagnetic wave detectors with different detection wavelengths receives and detects an electromagnetic wave L2, the wavelength absorbed by the gas can be identified. Thus, it is possible to identify the kind of the gas in the gas introduction mechanism 600.

The gas analyzing apparatus 2000 can be used, for example, for detecting carbon dioxide from a gas serving as an analysis target in order to give notice of danger, and for detecting alcohol from a gas serving as an analysis target in order to determine a drunk state. In particular, by using the electromagnetic wave detector array 1100 according to the fifth embodiment as the electromagnetic wave detector array 700, accuracy of a gas component analysis improves.

DESCRIPTION OF REFERENCE SYMBOLS

1 SUBSTRATE
2 CAVITY PORTION
3 SUPPORT LEG
4 DIELECTRIC LAYER
5 DETECTION FILM
6 THIN-FILM METAL WIRING
7 ALUMINUM WIRING
8 WAVELENGTH SELECTION STRUCTURE
10 TEMPERATURE DETECTION UNIT
11 RECESS
12 METAL PATTERN
13 INTERMEDIATE LAYER
14 METAL LAYER
15 METAL PATTERN
16 DIELECTRIC LAYER
17 METAL LAYER
18 MEMBRANE
19 METAL PATTERN
100 ELECTROMAGNETIC WAVE DETECTOR

The invention claimed is:

1. An electromagnetic wave detector selectively detecting an electromagnetic wave of a wavelength λA, the electromagnetic wave detector comprising:
a substrate including a cavity portion;
a temperature detection unit which includes:
a wavelength selection structure that generates a surface plasmon resonance with an electromagnetic wave of the wavelength λA which is predetermined, converts the electromagnetic wave into heat, and absorbs the heat, and
a detection film that detects the heat having been absorbed; and
a support structure which holds the temperature detection unit above the cavity portion, wherein
the support structure further includes a reflection structure which reflects an electromagnetic wave of an absorption wavelength of the support structure,
wherein the support structure is configured to include a support leg which includes an insulator layer, and the support leg includes a reflection structure which reflects an electromagnetic wave of an absorption wavelength of the insulator layer, and
wherein the reflection structure includes a plurality of metal patterns arranged on an upper side of the insulator layer of the support leg such that an electromagnetic wave of the absorption wavelength of the insulator layer causes surface plasmon resonance.

2. The electromagnetic wave detector according to claim 1, wherein the reflection structure is a MIM structure that includes the insulator layer of the support leg, a plurality of metal patterns that is arranged on an upper side of the insulator layer, and a metal layer that is disposed on a back side of the insulator layer, and an electromagnetic wave of the absorption wavelength of the insulator layer causes surface plasmon resonance.

3. The electromagnetic wave detector according to claim 1, wherein the wavelength selection structure includes a metal layer that has one of periodic recesses and periodic projections which are provided on a surface of the metal layer.

4. The electromagnetic wave detector according to claim 1, wherein the wavelength selection structure includes an intermediate layer that is configured to include one of an insulator, a semiconductor, and a dielectric, and periodic metal patterns that are provided on an upper side of the intermediate layer, and a metal layer that is provided on a back side of the intermediate layer.

5. The electromagnetic wave detector according to claim 4, wherein a horizontal cross-section of each of the periodic metal patterns has a shape selected from a group including a circular shape and a square shape.

6. The electromagnetic wave detector according to claim 4, wherein a horizontal cross-section of each of the periodic metal patterns has a shape selected from a group including a rectangular shape, an elliptical shape, and a polygonal shape.

7. The electromagnetic wave detector according to claim 4, wherein each of the periodic metal patterns is made of a material selected from a group including gold, silver, aluminum, and graphene.

8. An electromagnetic wave detector array comprising a plurality of the electromagnetic wave detectors according to claim 1, the electromagnetic wave detectors being in one of a one-dimensional arrangement and a two-dimensional arrangement.

9. The electromagnetic wave detector array according to claim 8, wherein at least two of the electromagnetic wave detectors are electromagnetic wave detectors which selectively detect electromagnetic waves of wavelengths that are different from each other.

10. A gas analyzing apparatus detecting a wavelength that is absorbed by a gas and identifying the gas, the gas analyzing apparatus comprising:
a light source which emits an electromagnetic wave;
a container which contains a gas that serves as an analysis target; and
at least one electromagnetic wave detector of claim 1, which receives an electromagnetic wave, wherein
an electromagnetic wave that is emitted from the light source is detected by the at least one electromagnetic wave detector after the electromagnetic wave passed through the gas in the container.

11. The gas analyzing apparatus according to claim 10, wherein the at least one electromagnetic wave detector includes a plurality of electromagnetic wave detectors that is in one of a one-dimensional arrangement and a two-dimensional arrangement.

12. The gas analyzing apparatus according to claim 10, wherein the gas that serves as the analysis target contains alcohol, and alcohol concentration in the gas is detected.

13. An electromagnetic wave detector selectively detecting an electromagnetic wave of a wavelength λA, the electromagnetic wave detector comprising:
a substrate including a cavity portion;
a temperature detection unit which includes:
a wavelength selection structure that generates a surface plasmon resonance with an electromagnetic wave of the wavelength λA which is predetermined, converts the electromagnetic wave into heat, and absorbs the heat, and
a detection film that detects the heat having been absorbed; and
a support structure which holds the temperature detection unit above the cavity portion, wherein
the support structure further includes a reflection structure which reflects an electromagnetic wave of an absorption wavelength of the support structure,
wherein the support structure is configured to include a membrane which is provided on the substrate, and the membrane includes a reflection structure which reflects an electromagnetic wave of an absorption wavelength of the membrane, wherein a support leg that contains an insulator layer is provided on the membrane, and the support leg further includes a reflection structure which reflects an electromagnetic wave of an absorption wavelength of the insulator layer and wherein the reflection structure includes a plurality of metal patterns arranged on an upper side of the insulator layer of the support leg such that an electromagnetic wave of the absorption wavelength of the insulator layer causes surface plasmon resonance.

14. The electromagnetic wave detector according to claim 13, wherein the reflection structure includes a plurality of metal patterns arranged on an upper side of the membrane such that an electromagnetic wave of the absorption wavelength of the membrane causes surface plasmon resonance.

15. The electromagnetic wave detector according to claim 13, wherein the reflection structure is a MIM structure that includes the membrane, a plurality of metal patterns that is arranged on an upper side of the membrane, and a metal layer that is disposed on a back side of the membrane, and an electromagnetic wave of the absorption wavelength of the membrane causes surface plasmon resonance.

16. The electromagnetic wave detector according to claim 13, wherein the wavelength selection structure includes a metal layer that has one of periodic recesses and periodic projections which are provided on a surface of the metal layer.

17. The electromagnetic wave detector according to claim 13, wherein the wavelength selection structure includes an intermediate layer that is configured to include one of an insulator, a semiconductor, and a dielectric, and periodic metal patterns that are provided on an upper side of the intermediate layer, and a metal layer that is provided on a back side of the intermediate layer.

18. The electromagnetic wave detector according to claim 17, wherein a horizontal cross-section of each of the periodic metal patterns has a shape selected from a group including a circular shape and a square shape.

19. The electromagnetic wave detector according to claim 17, wherein a horizontal cross-section of each of the periodic metal patterns has a shape selected from a group including a rectangular shape, an elliptical shape, and a polygonal shape.

20. The electromagnetic wave detector according to claim 17, wherein each of the periodic metal patterns is made of a material selected from a group including gold, silver, aluminum, and graphene.

* * * * *